United States Patent [19]
Cunningham

[11] 3,972,778
[45] Aug. 3, 1976

[54] APPARATUS FOR DETERMINING THE CONCENTRATION OF MICROORGANISMS
[76] Inventor: William Eric Cunningham, Ottawa, Canada
[22] Filed: Nov. 8, 1973
[21] Appl. No.: 413,929

[30] Foreign Application Priority Data
Nov. 17, 1972 Canada.................................. 156789

[52] U.S. Cl........................... 195/139; 195/103.5 R; 195/127
[51] Int. Cl.².......................................... C12K 1/04
[58] Field of Search................. 195/103.5, 127, 139

[56] References Cited
UNITED STATES PATENTS
3,129,144  4/1964  Page et al........................... 195/139
3,669,358  6/1972  Waldman............................ 195/127

Primary Examiner—David M. Naff
Assistant Examiner—R. B. Penland
Attorney, Agent, or Firm—Wood, Herron & Evans

[57] ABSTRACT

A method of, and apparatus for, the detection of particles or organisms, particularly faecal coliform, in which the fluid under test is dispensed drop-by-drop onto a moving absorbent surface. The surface is of such a nature, and/or is so treated that the organisms form discrete visible colonies which can be counted photo-electrically after incubation.

13 Claims, 1 Drawing Figure

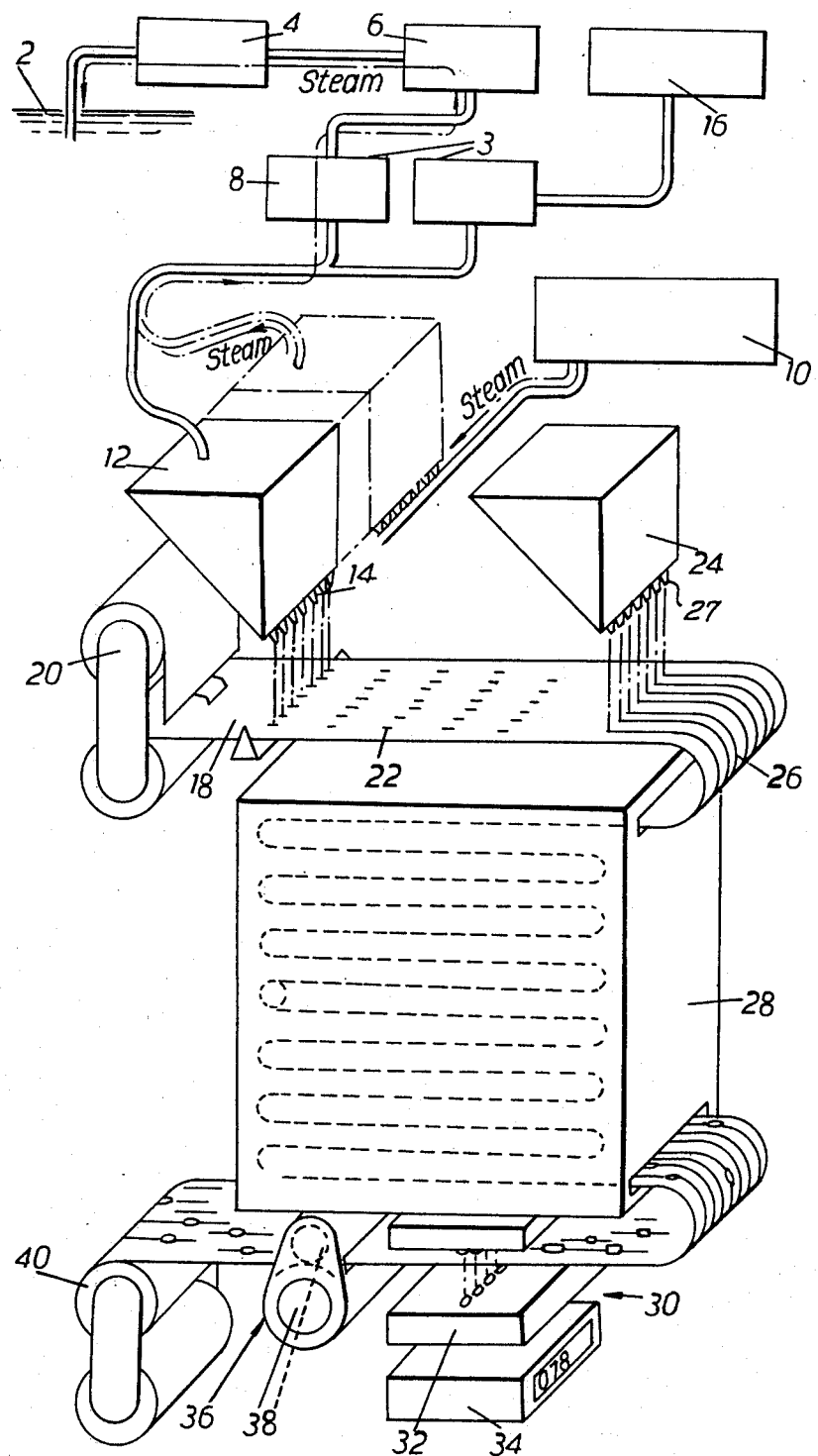

APPARATUS FOR DETERMINING THE CONCENTRATION OF MICROORGANISMS

This invention relates to the detection of small quantities of impurities in water supplies for example. It is particularly concerned with the detection of pollution by bacteria such as faecal coliform.

Known methods for detection of bacterial pollution are exceedingly laborious and time consuming and subject to serious human error. The general method normally employed may be described briefly as follows:

Samples of the liquid are collected in bottles and are shipped to the laboratory for analysis. At the laboratory the liquid samples are diluted and known volumes of the solution are poured into special vessels in the bottom of which are fitted millipore filters varying in size, typically 3 ins. dia. by 3/16 in. thick.

The solution is filtered with the aid of a vacuum or pressure pump and the bacteria present are trapped within the pores of the filter material, at this stage it should be noted that although bacteria are present on and within the fabric of the filter plates, they are much too minute to be visible to the naked eye.

After filtering, the filter plates on which the bacteria are trapped, are removed from the vessels and are placed on Petri dishes containing suitable nutrient for the bacteria, Each Petri dish with nutrient, filter plate and bacteria is then stored in an incubator which is suitably temperature and humidity controlled. Since a large number of filter plates are employed, special racks and trays are used to facilitate storage and retrival. After a period of approximately 24 hours, the Petri dishes and filter plates are removed from the incubator.

Next follows the tedious procedure of careful visual hand counting of the bacterial colonies which have developed on the filter plates and are now clearly visible in the form of dark round spots. Since each plate may contain 100 or more bacterial colonies scattered at random over the surface of the plate, and since in many instances the colonies overlap one another, considerable care is required during the count. Furthermore, since for statistical accuracy many plates must be used, the hard counting process (typically 2 to 5 minutes per plate) is tiring and is subject to significant human error.

Following the count, statistical formulae and tables are employed to estimate the concentration of the bacteria in the original liquid samples.

The above description applies to the method most commonly employed in the determination of bacterial concentration in liquids. Other methods make use of special solutions in test tubes and the measuring of PH values or the scattering effect on light due to the presence or growth of bacterial colonies within the solutions. Sometimes partial automation is employed to speed the process of handling of filter plates, test tubes, etc. Several photo electrical devices also exist largely in the experimental stage, which employ flying spot techniques to try to automate the counting of bacterial colonies on filter plates. However, the random distribution of colonies on the plates make accurate counting very difficult and necessitate complex expensive equipment.

A method in accordance with the invention for the detection of low concentrations of particles or organisms in a fluid, comprises dispensing the fluid drop-by-drop onto an absorbent surface which is being moved at a sufficient rate to ensure that the drops remain separate, the surface being so treated before and/or after dispensing that a detectable change subsequently occurs in the surface where a drop containing a particle or organism has fallen.

Preferably, in the case of the detection of organisms such as bacteria the surface is also treated to promote the growth of the bacteria, by dispensing a nutrient on it which is favourable to the growth of the particular organisms to be detected. The surface may then if necessary, be passed into an incubator, so that a coloured patch will grow in each place where a drop has fallen which contained a bacterium. This method is particularly preferred when detecting faecal coliform. The surface preferably comprises a transluscent tape so that the resultant patches can be counted by passing the tape between a light source and a photo-cell-operated counter, or alternatively the tape may be opaque and the patches may then be counted by reflected light.

If necessary, the solution to be tested is diluted before it is dispensed onto the moving surface, to ensure that the concentration of organisms or particles is so low that not more than one particle is likely to be contained in a single drop.

Apparatus in accordance with the invention, for the determination of the concentration of particles or organisms in a solution, therefore comprises a container having dropper means mounted above a moveable support adapted to carry an absorbent drop receiving surface, the support means being moveable at such a rate, and the absorbency of the surface being such, as to ensure that drops falling on the surface will remain separate.

The moveable support preferably comprises a system of rollers and the absorbent drop-receiving surface preferably comprises a continuous tape. Preferably, the apparatus further comprises incubator means through which the tape is then passed to stimulate growth of the organisms. The apparatus is preferably arranged so that the process can be carried out continuously, a long tape being arranged to pass, first beneath the dropper means, then through an incubator, and finally through a photo-cell detector to detect the presence of patches of bacterial growth.

The apparatus preferably further includes electronic counting and display means arranged to indicate the bacterial "count" in the fluid under test.

In a preferred embodiment of the invention, which incorporates an array of sensitive photo-electric cells as a counting device, the arrangement may be such that the bacterial colonies are incubated for less than the normal 24 hours since the presence of the colonies can be detected more readily by measuring electronically the change in opacity of the tape in the region carrying a colony, than by a manual counting process. The apparatus is preferably totally enclosed, so as to prevent contamination, and is arranged to be sterilised by means of steam.

In a preferred arrangement of the apparatus, which is adapted for the detection of bacteria, a tape forming the absorbent surface is first passed beneath a liquid dispenser which is arranged to distribute a controlled quantity of liquid in the form of parallel rows of drops onto the tape. A nutrient dispenser is arranged to subsequently dispense nutrient onto the tape in parallel rows coinciding with or covering the areas in which the drops of fluid have previously fallen.

Alternatively, the tape may be previously impregnated with nutrient, or another tape carrying the nutrient may be brought into contact with the first tape, during the incubation process.

One embodiment of the invention will now be described by way of example with reference to the accompanying drawings, which is a diagrammatic representation of the apparatus.

A liquid 2 which is to be analysed is pumped by a pump 4 through a filter 6 which is of a suitable size to remove relatively large unwanted particles from the fluid. A metering unit 8 is arranged to pass a known quantity of fluid, or to pass fluid at a preset rate, into a dispenser 12 which is provided with a row of droppers 14. At the same time a proportionate quantity of bacteria free fluid from a reservoir 16 may also be admitted into the dispenser, if it is required to dilute the fluid being measured. This may be necessary for reasons, explained below, if the concentration of bacteria is expected to be unusually high. A mixing chamber may be provided to ensure uniform distribution of the bacteria in the resulting solution.

The droppers 14 of the dispenser 12 are arranged in a row and an absorbent tape 18 supplied from a roller dispensing device 20 is arranged to pass beneath the droppers so that a number of parallel rows of spots 22 are produced on the tape. After passing beneath the droppers 14 the tape passes beneath a nutrient dispenser 24 which is arranged to supply small quantities of nutrient 26 onto the tape in parallel lines corresponding to the rows of spots 22 of fluid. The nutrient may be dispensed by dropper 27 as in the case of the fluid being tested, but the arrangement is in any case such that the nutrient is present over a sufficiently large area to cover all the spots.

The tape 22 is of sufficient width to allow a dry strip to remain on either side so that the tape can subsequently be guided through the apparatus by means of guides which engage its edges, to reduce the change of contamination of the apparatus.

After absorbing the fluid being tested, and the nutrient, the tape is guided through an incubator 28 through which it is guided in a sufficiently long path, and at a suitable speed, to enable bacterial colonies to develop to the stage where their presence can be detected by a photo-electric detector 30 by the time the tape leaves the incubator.

The detector 30 is arranged to project a number of beams of lights corresponding to the number of rows of dots on the tape, across the path of the tape towards a corresponding number of photo-electric cells comprising a sensing unit 32. The cells are connected in a suitable circuit configuration, for example by means of "OR" gates, to a counter circuit which operates a digital display 34, so that the total number of developed bacterial colonies on the tape is displayed on the counter.

The tape is driven through the apparatus by a drive 36 which comprises a constant speed motor and two sprung rollers 38 which engage the tape. A take-up reel 40 for the tape is also driven by the constant speed motor via a frictional clutch.

After use the apparatus is sterilised by passing steam through the dispensing vessel 12, the pump 4, the filter 6, and the meter 8, from a sterilising unit 10. In order to protect the tape from damage during the sterilising process, the dispenser 12 may be moveable to the dotted line position shown in the drawing so as to bring it well clear of the tape.

The apparatus is preferably provided, as shown, with a tape dispenser 20 which included two reels of tape providing automatic take-up of the second reel once the first reel has been exhausted. This obviates rethreading of tape through all the guides and rollers of the apparatus. Likewise the tape take-up unit 40 is preferably provided with two reels arranged so that when one reel is full, the tape is fed onto the other.

As an alternative to the replaceable tape shown, an endless belt constructed so as to be suitable for steam sterilisation may be used and the whole apparatus can then be filled with steam during the sterilisation process.

In the preferred embodiment of the invention, as discussed above, the conditions in the incubator and the speed of the tape transport are such that the bacterial colonies are developed as quickly as possible. To this end the incubator is preferably a substantially sealed, well-lagged enclosure so that suitably uniform temperature and humidity conditions can be maintained inside it. The tape is preferably arranged to run to and fro many times over a system of rollers so that a suitably long "Dwell-time" in the incubator is ensured, in a relatively small space.

The major advantage of the preferred embodiment of the invention is that the bacterial colonies are developed on the tape is an orderly pattern, rather than at random, which greatly simplifies the problem of counting them. Also, since the method does not rely on filtering techniques, there is little danger of minute organisms or particles escaping detection. This is particularly important in the case of detection of bacteria such as faecal coliform, when testing water supplies for contamination. Although the embodiment described uses an electronic counter, it will be appreciated that this type of arrangement would also render manual counting easier, in a less sophisticated form of the apparatus.

I claim:

1. Apparatus for determining the concentration of organisms in a sample of fluid comprising
    an absorbent drop-receiving surface,
    dropper means adapted to discharge single drops of said fluid onto said drop-receiving surface,
    movable support means adapted to carry said absorbent drop-receiving surface beneath said dropper means, said support means being movable at such a rate as to insure that fluid drops discharged onto said drop-receiving surface remain separate one from the other,
    photo-electric detector means positioned sufficiently downstream of said dropper means to detect any changes in light reflection or transmission characteristics of each separate drop as so caused by the presence of said organisms after exposure of said organisms to suitable incubation conditions, and
    counter means connected with said detector means, said counter means registering the cumulative total of said separate drops in which any change of light reflection or transmission characteristics has been detected, thereby permitting the concentration of organisms within said fluid to be determined.

2. Apparatus as claimed in claim 1 further comprising,
    a nutrient dispenser arranged to supply nutrient to that area of said drop-receiving surface which receives the drops of fluid, said nutrient being adapted to promote the growth of colonies of said organisms.

3. Apparatus as claimed in claim 1 in which said drop-receiving surface is pre-impregnated with nutrient to promote the growth of said organisms.

4. Apparatus as claimed in claim 1 in which said drop-receiving surface comprises a disposable tape.

5. Apparatus as claimed in claim 4 in which said movable support means comprises a system of rollers and guides.

6. Apparatus as claimed in claim 1 including a plurality of droppers arranged to dispense said fluid in rows of drops extending across said drop-receiving surface.

7. Apparatus as claimed in claim 1 further comprising
an incubator through which said drop-receiving surface is moved by said movable support means, said incubator being adapted to provide suitable conditions for promoting the growth of colonies of said organisms.

8. Apparatus as claimed in claim 1 including
light beam projector means arranged on the opposite side of said drop-receiving surface from said photoelectric detector means, said detector means being adapted to measure the transmissivity of said drop-receiving surface.

9. Apparatus as claimed in claim 1 including light beam projector means arranged on the same side of said drop-receiving surface as said photo-electric detector means, said detector means being adapted to measure the reflectivity of said drop-receiving surface.

10. Apparatus as claimed in claim 4 in which said movable support means further comprises
an automatic tape feed adapted to connect a fresh tape to the end of a used tape, thereby permitting said apparatus to be kept in operation without downtime for rethreading a new tape.

11. Apparatus as claimed in claim 1 in which said drop-receiving surface comprises an endless belt.

12. Apparatus as claimed in claim 1 wherein a nutrient is continuously supplied onto said drop-receiving surface, thereby forming a continuous line of nutrient that insures said nutrient will contact all of said fluid drops on said drop-receiving surface.

13. Apparatus for determining the concentration of organisms in a sample of fluid comprising
an absorbent drop-receiving surface,
dropper means adapted to discharge single drops of said fluid onto said drop-receiving surface,
means for supplying nutrient to said organisms,
movable support means adapted to carry said absorbent drop-receiving surface beneath said dropper means, said support means being movable at such a rate as to insure that fluid drops discharged onto said drop-receiving surface remain separate one from the other,
incubator means for exposing said drop-receiving surface to suitable organism incubation conditions,
photo-electric detector means positioned sufficiently downstream of said dropper means to detect any changes in light reflection or transmission characteristics of each separate drop as so caused by the presence of said organisms, and
counter means connected with said detector means, said counter means registering the cumulative total of said separate drops in which any change of light reflection or transmission characteristics has been detected, thereby permitting the concentration of organisms within said fluid to be determined.

* * * * *